United States Patent [19]

Takahashi

[11] Patent Number: 5,014,685

[45] Date of Patent: May 14, 1991

[54] BRAKE FOR BENDING CONTROL DEVICE OF ENDOSCOPE

[75] Inventor: Nagashige Takahashi, Tokyo, Japan

[73] Assignee: Asahi Kogaku Kogyo Kabushiki Kaisha, Tokyo, Japan

[21] Appl. No.: 373,529

[22] Filed: Jun. 30, 1989

[30] Foreign Application Priority Data

Jul. 13, 1988 [JP] Japan .................................. 63-176082

[51] Int. Cl.$^5$ ............................................... A61B 1/00
[52] U.S. Cl. ................................................... 128/4
[58] Field of Search ......................... 128/4–8; 138/120

[56] References Cited

U.S. PATENT DOCUMENTS

| | | | |
|---|---|---|---|
| 3,557,780 | 1/1971 | Sato | 128/4 |
| 3,788,303 | 1/1974 | Hall | 128/4 |
| 3,892,228 | 7/1975 | Mitsui | 128/4 |
| 4,078,555 | 3/1978 | Takahashi | 128/4 |
| 4,203,430 | 5/1980 | Takahashi | 128/4 |
| 4,461,282 | 7/1984 | Ouchi et al. | 128/4 |
| 4,483,326 | 11/1984 | Yamaki | 128/4 |
| 4,617,914 | 10/1986 | Ueda | 128/4 |

Primary Examiner—Benjamin Layno
Attorney, Agent, or Firm—Sandler, Greenblum & Bernstein

[57] ABSTRACT

A brake for a bending control device of an endoscope comprising a driving device rotatably provided in a control part for pulling a control wire, a rotary shaft rotating together with the driving device, a fixed shaft fixed in the control part in concentrical relation to the rotary shaft, a friction member accommodating chamber defined in an annular shape between the fixed and rotary shafts, and a resilient friction member loaded within the friction member accommodating chamber in a compressed state. When the control wire is pulled by rotating the driving device, the rotary shaft rotates together with the driving device. As a result, friction resistance occurs between the friction member loaded in the friction member accommodating chamber on the one hand and the rotary and fixed shafts on the other, thus applying the brakes to the driving device.

12 Claims, 2 Drawing Sheets

BRAKE FOR BENDING CONTROL DEVICE OF ENDOSCOPE

BACKGROUND OF THE INVENTION

1. Field of the Invention

The present invention relates to a brake for a bending control device of an endoscope and, more particularly, to a brake for an endoscope bending control device of the type wherein a driver that pulls a bending control wire is braked by means of frictional force to maintain the bendable portion of the endoscope in a desired bent state.

2. Description of the Related Art

The bending control device of an endoscope includes a brake which is used to maintain the bendable portion of the endoscope in a desired bent state in order to fix the observation field of view. One type of conventional brake for endoscope bending control devices has heretofore been designed to fix the bendable portion in a desired bent position.

However, not considerably inconvenient if it is impossible to vary the angle of bending of the bendable portion after it has been fixed in a particular bent position. Therefore, it is common practice to employ brakes of the type wherein a driver that pulls a bending control wire is braked by means of frictional force so that it is possible not only to maintain the bendable portion in a desired bent state but also to vary the angle of bending after it has been fixed in a particular bent position.

A typical conventional brake of the type described above has heretofore been arranged such that a rotary disk having a plastic or cork material attached thereto is pressed against a fixed disk to produce frictional force to thereby maintain the bendable portion in a desired bent state.

This type of conventional brake suffers, however, from the disadvantage that the diameter of the disks must be increased in order to obtain large frictional force and this leads to an increase in the size of the control part, so that the operability is deteriorated and the mechanism is complicated.

In the bending control devices of endoscopes, the greater the angle of bending of the bendable portion, the greater the resilient force acting on the bendable portion, that is, the greater the force acting on the bendable portion trying to restore it to its straight position. However, the conventional brake structure, having a rotary disk merely pressed against a fixed disk, has no consideration for the relationship between the level of frictional force produced and the magnitude of bending angle. Therefore, if the frictional force is set at a level which will be convenient for the operation, when the bendable portion is bent at a relatively great angle, the frictional force produced cannot resist the resilient force acting on the bendable portion, thus causing the bendable portion to be undesirably restored to its straight position.

If the frictional force of the conventional brake structure is increased so that the bendable portion, when bent at a relatively great angle, will not undesirably be restored to its straight position, the level of frictional force will be excessively high when the bendable portion is close to its straight position. Thus, it will be impossible to conduct smoothly the operation of varying the angle of bending.

SUMMARY OF THE INVENTION

An object of the present invention is to provide a brake for a bending control device of an endoscope which is designed so that it is possible, with a small and simple mechanism to maintain the bendable portion in position when bent at a relatively great angle, and also to provide a braking operation even when the bendable portion is close to its straight position which still allows excellent operability.

Other objects and advantages of the present invention will become apparent from the following detailed description of an illustrated embodiment of the invention.

According to the present invention, there is provided a brake for a bending control device of an endoscope comprising: a driving device rotatably provided in a control part for pulling a control wire; a rotary shaft rotating together with the driving device; a fixed shaft fixed in the control part in concentrical relation to the rotary shaft; a friction member accommodating chamber defined in an annular shape between the fixed and rotary shafts; and a resilient friction member loaded within the friction member accommodating chamber in a compressed state.

In addition, there is provided a brake for a bending control device of an endoscope comprising: a driving device rotatably provided in a control part for pulling a control wire; a rotating device rotating together with the driving device; and a frictional resistance applying device for applying to the rotating device frictional resistance the magnitude of which varies in accordance with the amount of rotation of the rotating device.

In addition, there is provided a brake for a bending control device of an endoscope comprising: a driving device for driving a bendable portion of the endoscope so that the bendable portion is bent as desired; a rotary shaft rotating together with the driving device; a fixed shaft fixed in the control part coaxially to the rotary shaft; a friction member accommodating chamber defined between the fixed and rotary shafts; a resilient friction member loaded within the friction member accommodating chamber; and a device for adjusting the magnitude of friction caused by the resilient friction member.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

Figure 1:
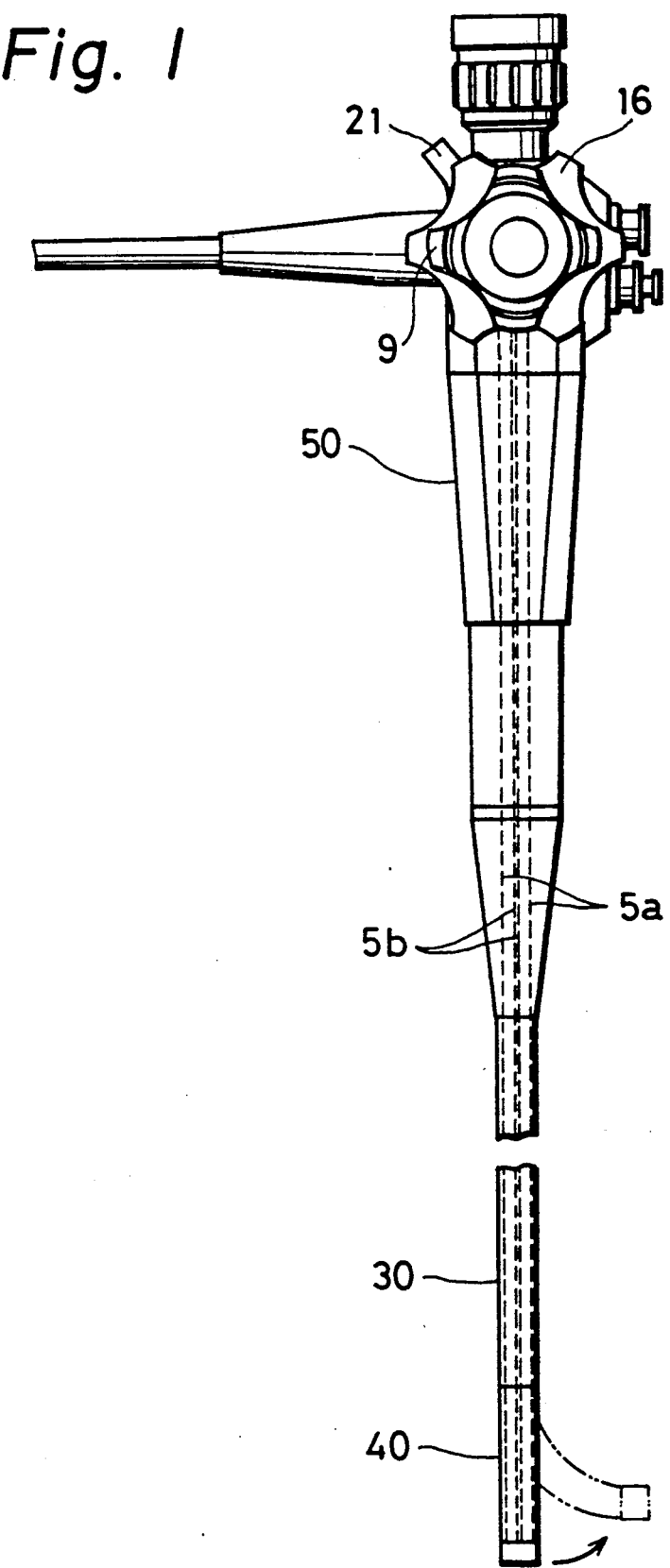
FIG. 1 is a side view of an endoscope to which one embodiment of the present invention is applied.

Referring to FIG. 1, which shows the general arrangement of an endoscope, an insert part 30 which is sheathed with a flexible tube has a bendable portion 40 formed at the distal end thereof, and a control part 50 is connected to the proximal end of the insert part 30. A pair of up and down control wires (UD control wires) 5a and a pair of right and left control wires (RL control wires) 5b extend from the bendable portion 40 to the control part 50 through the insert part 30.

The proximal end portion of each of the control wires 5a and 5b is connected to a bending control device which is provided in the control part 50. The control wires 5a and 5b are pulled by turning an up and down bending control knob (UD control knob) 16 and a right and left bending control knob (RL control knob) 9 which are projectingly provided on the control part 50, thereby enabling the bendable portion 40 to be bent in a desired direction and at a desired angle.

Figure 2:
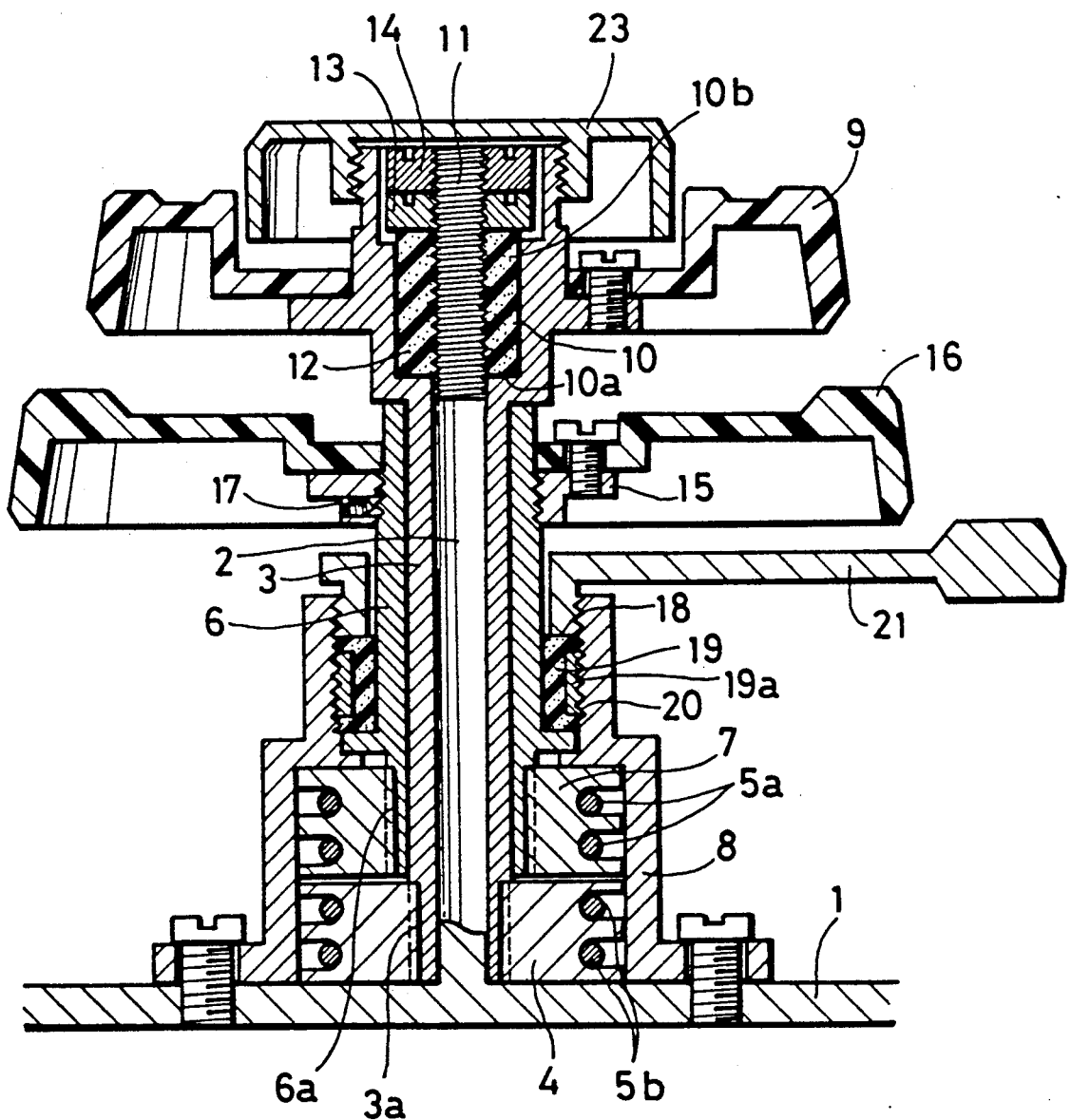
FIG. 2 is a sectional view of the bending control device according to the embodiment.

Referring next to FIG. 2, which shows the bending control device, the reference numeral 1 denotes a base which is secured in the control part 50. A rod-shaped fixed shaft 2 stands on the base 1, the shaft 2 being formed integral with the base 1. A rotary shaft (RL rotary shaft) 3 for right and left bending control is rotatably fitted on the fixed shaft 2. A pulley 4 is connected to a square shaft portion 3a having a square cross-section which is formed on the lower end portion of the RL rotary shaft 3 so that the pulley 4 rotates together with the rotary shaft 3 as one unit. The RL control wires 5b are wound around the pulley 4, so that, as the pulley 4 is rotated, the RL control wires 5b are pulled and the bendable portion 40 is thereby bent rightward or leftward.

A rotary shaft (UD rotary shaft) 6 for up and down bending control is rotatably fitted on the outer periphery of the RL rotary shaft 3, and a pulley 7 is connected to a square shaft portion 6a having a square cross-section which is formed on the lower end portion of the UD rotary shaft 6 so that the pulley 7 rotates together with the rotary shaft 6 as one unit. The UD control wires 5a are wound around the pulley 7, so that, as the pulley 7 is rotated, the UD control wires 5a are pulled and the bendable portion 40 is thereby bent upward or downward.

Further, a tubular fixed shaft 8 is fixed to the base 1 in such a manner as to surround the two pulleys 4 and 7, thus covering the pulleys 4 and 7 so that the control wires 5a and 5b will not come off the outer peripheries of the pulleys 4 and 7. The peripheral wall of the fixed shaft 8 is partially cut and the control wires 5a and 5b are drawn out through the cut portion (not shown).

The RL control knob 9 for right and left bending control is screwed to the projecting end portion of the RL rotary shaft 3, so that it is possible to effect right and left bending control by turning the RL control knob 9. An annular friction member accommodating chamber 10 is defined between the projecting end portion of the fixed shaft 2 and the RL rotary shaft 3. More specifically, the distal end portion of the RL rotary shaft 3 is cut in the form of a spot facing so that the inner diameter of this portion is larger than that of the other portion of the rotary shaft 3, thereby forming the bottom 10a and outer wall surface 10b of the friction member accommodating chamber 10. A thread groove 11 is cut in the outer peripheral surface of that portion of the fixed shaft 2 which extends from the bottom of the friction member accommodating chamber 10 to the distal end of the shaft 2.

A resilient friction member 12 which is in the form of a tube is loaded within the friction member accommodating chamber 10 in a compressed state by being pressed by means of a nut 13. The friction member 12 may be formed from a resilient material, for example, a chloroprene rubber material or an olefin thermoplastic elastomer, which has a suitable hardness imparted thereto. The degree to which the friction member 12 is compressed can be adjusted by varying the degree to which the nut 13 is tightened. The reference numeral 14 denotes a fixed nut for locking the nut 13 from rotating, while the numeral 23 denotes a cover which is threaded to the distal end portion of the RL rotary shaft 3.

The friction member 12 that is pressed within the friction member accommodating chamber 10 by means of the nut 13 has frictional resistance to the RL rotary shaft 3 at the area of contact between the same and the bottom 10a and outer wall surface 10b of the friction member accommodating chamber 10. The friction member 12 also has frictional resistance at the area of contact between the same and the threaded outer peripheral surface of the fixed shaft 2 and the lower surface of the nut 13. Accordingly, when the bendable portion 40 is bent rightward or leftward by turning the RL control knob 9, frictional resistance occurs between the RL rotary shaft 3 rotating at that time and the fixed shaft 2 and the nut 13, which are fixed members, through the friction member 12 interposed therebetween. This frictional resistance brakes the rotation of the pulley 4, so that the bendable portion 40 is maintained in a desired bent state. However, if the RL control knob 9 is turned against the frictional resistance, the pulley 4 can be rotated to effect bending control.

In addition, the friction member 12 is in thread engagement with the thread groove 11 provided in the outer periphery of the distal end portion of the fixed shaft 2. Therefore, when rotating, the friction member 12 is urged to move axially by the action of thread, so that, when moving downward, the friction member 12 is strongly pressed against the bottom 10a of the friction member accommodating chamber 10, whereas, when moving upward, the friction member 12 is strongly pressed against the lower surface of the nut 13, thus increasing the level of contact pressure acting on these portions. Since the frictional resistance between the friction member 12 and the RL rotary shaft 3 is generally greater than that between the friction member 12 and the fixed shaft 2, the friction member 12 rotates together with the RL rotary shaft 3 and, as the angle of rotation increases, the friction member 12 is pressed against either the bottom 10a of the friction member accommodating chamber 10 or the lower surface of the nut 13, thus increasing the frictional resistance.

As the angle of bending increases, the level of resilient force acting on the bendable portion 40, trying to restore it to its straight position, increases. However, in this embodiment wherein the friction member 12 is in thread engagement with the thread groove 11, as the bending angle increases, the frictional resistance (that is, the braking force) increases as described above. It is therefore possible to maintain the bendable portion 40 in a desired bent state even when it is bent at a relatively great angle. Since the frictional resistance that occurs when the bendable portion 40 is bent at a small angle is relatively small, it is possible to effect a smooth bending operation.

It should be noted that it is possible to obtain a level of frictional force which is substantially equal to that in the prior art by employing a structure wherein the thread groove 11 that is in thread engagement with the friction member 12 is not provided and the friction member 12 is merely loaded within the friction member accommodating chamber 10 in a compressed state.

The UD control knob 16 for up and down bending control is screwed to the UD rotary shaft 6 through a connecting nut 15. The reference numeral 17 denotes a small screw for fixing the connecting nut 15 so that the nut 15 will not rotate relative to the UD rotary shaft 6. An annular friction member accommodating chamber 18 is defined between the fixed shaft 8 and the UD rotary shaft 6, and a resilient friction member 19 which is in tubular form is loaded within the friction member accommodating chamber 18 in a compressed state. The friction member 19 has a metal ring 19a provided on the outer peripheral portion thereof in one unit, the metal ring 19a having a thread groove cut in the outer wall surface thereof.

A thread groove 20 is cut in the inner peripheral surface of that portion of the fixed shaft 8 that faces the friction member accommodating chamber 18. The thread groove 20 is in thread engagement with the metal ring 19a and a nut 21 with a lever which compresses the friction member 19 from the upper side thereof. Accordingly, the degree to which the friction member 19 is compressed can be adjusted by turning the nut 21 by a manual operation. The metal ring 19a is reliably thread-engaged with the fixed shaft 8, and the friction member 19 is compressed vertically by virtue of the thread engagement in response to the rotation of the UD rotary shaft 6. Thus, the rotation of the pulley 7 for up and down bending control can be braked by means of frictional resistance in the same way as in the case of the above-described right and left bending control.

According to the present invention, a brake for an endoscope bending control device is realized simply by loading a friction member into a friction member accommodating chamber in a compressed state. It is therefore possible to simplify the structure and also reduce the size and weight of the brake. If the friction member is thread-engaged with a thread groove, the frictional resistance increases and hence the braking force increases as the angle of bending increases. Therefore, even when the bendable portion is bent at a great angle, it can be reliably maintained in this bent portion. When the bendable portion is bent at a small angle, the frictional resistance decreases, so that it is possible to effect a smooth bending operation.

Further, it is easy to realize a waterproof structure and hence possible to prevent fluctuation of the frictional resistance due to leakage of water or the like.

While the invention has been described by reference to a specific embodiment chosen for purposes of illustration, it should be apparent that numerous modifications could be made thereto by those skilled in the art without departing from the basic concept and scope of the invention.

What is claimed is:

1. A brake for a bending control device of an endoscope comprising:
    driving means rotatably provided in a control part for pulling a control wire;
    a rotary shaft rotating together with said driving means;
    a fixed shaft fixed in said control part in concentric relation to said rotary shaft;
    a friction member accommodating chamber defined in an annular shape between said fixed and rotary shafts; and
    a resilient friction member loaded within said friction member accommodating chamber in a compressed state.

2. A brake for a bending control device of an endoscope having a bendable portion extending at an angle relative to said bending control device, said bending control device comprising:
    driving means rotatably provided in a control part for pulling a control wire, said control wire controlling the angle of said bendable portion;
    rotating means rotating together with said driving means; and
    frictional resistance applying means for applying frictional resistance to said rotating means, the magnitude of said frictional resistance varying in accordance with the amount of rotation of said rotating means.

3. A brake for a bending control device of an endoscope according to claim 2, wherein said frictional resistance increases as the angle of bending increases.

4. A brake for a bending control device of an endoscope comprising:
    driving means for driving a bendable portion of said endoscope so that said bendable portion is bent as desired;
    a rotary shaft rotating together with said driving means;
    a fixed shaft in a control part coaxially to said rotary shaft;
    a friction member accommodating chamber defined between said fixed and rotary shafts; and
    a resilient friction member loaded within said friction member accommodating chamber;
    wherein said friction member generates frictional resistance between said friction member and a wall surface of said frictional member accommodating chamber, said wall surfaces positioned perpendicular to the shafts.

5. A brake for a bending control device of an endoscope comprising:
    driving means rotatably provided in a control part for pulling a control wire;
    a rotary shaft rotating together with said driving means;
    a fixed shaft fixed in said control part in concentric relation to said rotary shaft;
    a friction member accommodating chamber defined in an annular shape between said fixed and rotary shafts; and
    a resilient friction member loaded within said friction member accommodating chamber in a compressed state;
    wherein said friction member generates frictional resistance between said friction member and a wall surface of said frictional member accommodating chamber, said wall surface positioned perpendicular to the shafts.

6. A brake for a bending control device of an endoscope according to claim 5, wherein said driving means is a pulley which is connected to an operating means for a manual operation.

7. A brake for a bending control device of an endoscope according to claim 5, further comprising means for adjusting the degree to which said friction member is compressed.

8. A brake for a bending control device of an endoscope according to claim 7, wherein said means for adjusting the degree to which said friction member is compressed is a nut.

9. A brake for a bending control device of an endoscope according to claim 7, wherein said means for adjusting the degree to which said friction member is compressed enables said degree of compression to be adjusted by a manual operation.

10. A brake for a bending control device of an endoscope according to claim 7, wherein a thread groove is formed in the peripheral surface of that portion of said fixed shaft which faces said friction member accommodating chamber, said friction member being provided so as to be in thread engagement with said thread groove.

11. A brake for a bending control device of an endoscope according to claim 10, wherein the frictional resistance between said friction member and said rotary shaft is greater than that between said friction member and said fixed shaft, so that said friction member rotates together with said rotary shaft.

12. A brake for a bending control device of an endoscope according to claim 5, wherein said friction member is in the form of a tube.

* * * * *

UNITED STATES PATENT AND TRADEMARK OFFICE
CERTIFICATE OF CORRECTION

PATENT NO. : 5,014,685
DATED : May 14, 1991
INVENTOR(S) : N. Takahashi

It is certified that error appears in the above-identified patent and that said Letters Patent is hereby corrected as shown below:

```
Column 1, line 23, "not" should be --it is --.
Column 1, line 23, "if it is" should be --if not--.
Column 2, line 6,  after "mechanism" insert --,--.
```

Signed and Sealed this

Eighth Day of June, 1993

Attest:

MICHAEL K. KIRK

Attesting Officer

Acting Commissioner of Patents and Trademarks